United States Patent
Tramontana (12)

(10) Patent No.: US 6,284,261 B1
(45) Date of Patent: *Sep. 4, 2001

(54) DISPOSABLE ABSORBENT ARTICLE CONTAINING AN ESSENTIAL OIL

(75) Inventor: Priscilla M. Tramontana, Yardville, NJ (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,975

(22) Filed: May 27, 1999

Related U.S. Application Data

(60) Provisional application No. 60/088,962, filed on Jun. 11, 1998.

(51) Int. Cl.⁷ .............. A61F 6/06; A61F 13/02; A61K 31/22
(52) U.S. Cl. .......... 424/430; 424/431; 514/546; 514/967
(58) Field of Search ............... 424/159.1, 430, 424/431; 514/546, 967

(56) References Cited

U.S. PATENT DOCUMENTS

| | | | |
|---|---|---|---|
| 3,688,985 | 9/1972 | Engel | 239/54 |
| 4,237,591 | 12/1980 | Ginocchio | 28/121 |
| 4,343,783 * | 8/1982 | Hooper et al. | 424/28 |
| 5,306,487 | 4/1994 | Karapasha et al. | 424/76.6 |
| 5,607,754 * | 3/1997 | Giles et al. | 428/211 |
| 5,733,272 | 3/1998 | Brunner et al. | 604/359 |
| 5,939,050 * | 8/1999 | Iyer et al. | 424/49 |

FOREIGN PATENT DOCUMENTS

| | | |
|---|---|---|
| 1083145 | 2/1994 | (CN) . |
| 3331573 A1 | 3/1985 | (DE) . |
| 4136540 A1 | 5/1992 | (DE) . |
| 57601 | 12/1991 | (HU) . |
| 212933 | 2/1997 | (HU) . |
| WO8905661 A1 | 6/1989 | (WO) . |
| WO9725106 A1 | 7/1997 | (WO) . |
| WO9738738 A1 | 10/1997 | (WO) . |

* cited by examiner

Primary Examiner—Kevin E. Weddington

(57) ABSTRACT

The invention relates to disposable absorbent articles containing an additive to control odors associated with bodily fluids. The invention is particularly useful in articles used to manage urine and menstrual fluids. The single additive provides both a pleasant aroma and antimicrobial activity.

7 Claims, No Drawings

DISPOSABLE ABSORBENT ARTICLE CONTAINING AN ESSENTIAL OIL

This is a Continuation-in-Part (CIP) of prior application Ser. No.: 60/088,962, filed Jun. 11, 1998.

FIELD OF THE INVENTION

The present invention relates to a disposable absorbent article containing a fragrant emitting and microbe inhibiting additive, and methods for making the same. The additives are essential oils and/or derivatives thereof.

BACKGROUND OF THE INVENTION

There are two common forms of disposable articles that are designed to absorb menstrual fluids discharged from a female's cervix. The first article is intended to be wholly inserted into the vaginal canal, and positioned near or against the cervical os. These articles are commonly referred to as catemenial tampons, or simply tampons. Some of the disadvantages related to tampons are the following: they can be attributed to excessive vaginal drying, they have been associated with toxic shock syndrome, they can be uncomfortable to insert and remove, especially on light flow days, and they have limited absorbing capacity, due to the regulations set by the U.S. Food and Drug Administration.

The second widely known and used article for collecting menstrual fluids is the sanitary napkin. This product is designed to be worn external to the vagina. Sanitary napkins can also be used to absorb urine, due to the size and positioning against the perineum. The product can be attached to the crotch of undergarments, attached directly to the vulvar region with body adhesives, and also worn partially or totally between the labia minora and majora. Many consumers choose to wear external absorbent articles because of their concern of toxic shock syndrome, they have difficulty inserting and removing tampons, they have difficulty wearing tampons, and they have a need for higher absorbing capacity than that available from tampons. As with tampons however, there are disadvantages that have been voiced by consumers who rely on external absorbing articles for their fluid management needs.

One perceived disadvantage of external sanitary napkins is their association with odors. Menstrual fluid contains a variety of substances including proteins and lipids. Microbial action on proteins has been recognized as a source of malodor. Urine is another fluid that can be absorbed by sanitary protection products, and microbial activity can form ammonia from urea in excreted urine. Consumers complain of not feeling "fresh" during their period, and hence seek out products that claim to control odor issues.

There have been a number of technologies developed for controlling odors associated with bodily fluids; particularly those attributed to perspiration, menstrual fluid degradation products, urine degradation products, and miscellaneous urine odors. Nearly all of the technologies can be placed into three main subcategories. The first is the use of added materials to absorb or adsorb volatile odors in an effort to restrict their release to the environment surrounding the consumer. Materials or compositions that adsorb and/or absorb volatile odors include sodium bicarbonate, sodium salts or ethylenediamine tetraacetic acid (EDTA), activated carbon, zeolites, and mixtures of sodium bicarbonate, EDTA, and activated carbon. These approaches are disclosed in U.S. Pat. No. 4,237,591 and 5,306,487. The second is the use of masking materials, such as perfumes, and the third is the use of substances to inhibit the production of bodily fluid degradation products. U.S. Pat. No. 5,733,272 discloses absorbent articles containing compositions of moisture-activated encapsulated perfumes and odor-controlling agents, including anti-microbial compounds.

The discussion thus far has highlighted technologies that are believed to remedy either malodors directly by inhibiting microbial activity, thereby decreasing the level of urine and menses degradation products, or indirectly by suppressing or overcoming the odors as they exist.

SUMMARY OF THE INVENTION

The object of the present invention is to utilize a single additive in disposable absorbent articles to both provide a pleasant aroma, and inhibit microbial growth. The single additive is an essential oil, derivative, or variation therefrom.

In accordance with one embodiment of the present invention, there has now been provided a disposable absorbent article containing an essential oil in an amount effective to provide a pleasant aroma and inhibit microbial growth.

In accordance with a second embodiment of the present invention there has been provided a method of making a disposable absorbent article containing an essential oil in an amount effective to provide a pleasant aroma and inhibit microbial growth comprising:

a) providing an absorbent material;
b) providing a liquid permeable material;
c) providing a liquid impermeable material;
d) encasing the absorbent material with the liquid permeable material and liquid impermeable material; and
e) contacting at least one of the absorbent material, the liquid permeable material, the liquid impermeable material, or a combination thereof with an essential oil.

DETAILED DISCUSSION OF THE INVENTION

The present invention is directed to a disposable absorbent article containing one or more essential oils. Essential oils are highly concentrated, volatile liquids originating from a single botanical source. A typical essential oil is a complex mixture of alcohols, aldehydes, esters, ketones, oxides, phenols and terpenes.

Essential oils can be extracted by steam distillation, and other techniques known in the art, from a variety of plant components, including, but not limited to, roots, leaves, bark, flowers and pulp. The majority of the oil-producing plants are represented by 90 species, and these are derived from about 30 different plant families.

The present invention provides an absorbent article containing one or more essential oils in an amount effective to provide two functions: emit a pleasant aroma, and inhibit microbial growth. Rosemary oil, clove oil, ginger oil, turmeric oil, chamomile oil, lemon grass oil, thyme oil, achillea oil, thulasi oil, clary sage oil, cedar (hinoki) oil, and derivatives, variations, and mixtures thereof, are all suitable for use as the essential oil. Synthetic forms of the oils described above can also be employed in the present invention. The preferred essential oil is rosemary oil, which is commercially available from Lorann Oils.

Malodors attributed to bodily fluids are most likely the result of bacteria degrading components residing in the bodily fluids. Bacteria can transform phospholipids into amines and fatty acids, and urea in urine to ammonia. Rosemary oil, for example, is an effective inhibitor of a number of gram positive and gram negative bacteria, such as, but not limited to *Staphylococcus aureus, Eschericia coli,* and *Pseudomonas aeruginosa.* Further to its inhibiting affect on bacteria, rosemary oil also has an inhibiting affect on a variety of fungi and yeast. Of particular interest to feminine hygiene, rosemary oil has been seen to inhibit the growth of *Candida albicans.*

In addition to its antimicrobial activity, rosemary oil emits a pine-like, camphorous odor. Synergistic odor control is thus achieved in that rosemary oil both inhibits the microbial growth that degrades bodily fluid components and provides a pleasant aroma.

The effectiveness of an essential oil as a fragrance may be determined by gathering organoleptic data from a panel presented with a series of absorbent article samples containing increasing concentrations of essential oil. The samples are then evaluated in a variety of environments, including but not limited to prior to wearing and during wearing. The panelists are asked a series of questions relating to their perceptions of the effectiveness of essential oil, at various add-on amounts, to provide an aroma.

Test methods for determining the amount of essential oil necessary to inhibit microbial growth include the following: analytical methods employed to investigate microbial growth in the presence of essential oil, and analytical/organoleptic methods employed to investigate the level of malodorous degradation products generated by microbial activity on cervical and urethral discharge As used herein, inhibition means substantially maintaining an existing microbe colony by the prevention of the additional growth of microbes. Inhibition does not require the killing of existing microbes or a reduction in size of the colony, although this is a possible result.

One test method that may be used to determine the microbial inhibition properties of essential oils is the zone of inhibition test. Another useful test method is the Durham's Fusion test. Those skilled in the art are familiar with other test methods in the microbiology community that can be used to determine microbial inhibition as described in the present invention.

In general, the amount of essential oil used in the absorbent article is between about 0.1 and about 8 weight percent, more preferably between about 0.2 and about 4 weight percent, and most preferably between about 0.5 and about 1.5 weight percent. Due to the relatively high volatility of essential oils, additional binder materials or mechanisms are preferably employed to reduce the premature loss of the essential oil once it has been added to the disposable absorbent article. (If compounding means are employed, then the level can be adjusted to yield a similar range of add-on available at the surface after migration has occurred.)

The disposable absorbent article of the present invention can take a plurality of forms including, but not limited to, sanitary napkins, tampons, diapers, surgical gowns, bedsheets, incontinence products, and wipes. The present invention is particularly advantageous for articles designed for managing cervical and urethral discharge. As used here, and throughout the text, sanitary napkin means any feminine hygiene product worn external to the vagina.

Essential oils can be added to any of the elements used in manufacturing disposable absorbent articles, during their individual manufacture, e.g., any one of the elements used in making the article is combined with essential oil prior to manufacturing the disposable absorbent article, or during their configuration into the article itself, or added to the final product once constructed from the elements.

One method of incorporating essential oils into the articles is by compounding the essential oils with a base polymer and then forming a film or fiber from the blend. These films or fibers can be used to form the elements utilized in the manufacture of disposable absorbent articles. Additives compounded into polymers, which then migrate at least partially to the surfaces of the solidified materials, are commonly referred to as "blooming agents." Blooming agents are known in the art to be useful in altering the surface of a material. A representative, non-limiting list of uses of blooming agents, include making the surface more lubricious, protecting the polymer from degradation, making the surface wettable, and making the surface releasable, as used in the molding business. A benefit of compounding the essential oil additives with a base polymer, is reducing the amount of additive lost, or lengthening the time elapsed before effective levels of essential oils are diminished, because of the migration and total separation from the base polymer that is required.

Another method of adding essential oils to materials used in disposable absorbent articles is to apply the essential oils to a finished product, typically by a coating means. Simplicity and efficiency are two benefits of using coating techniques. Coating means that can suitably be used in the present invention include, but are not limited to dip, slot, spray, melt blown, control coat, and swirl spray.

Sanitary napkins are commercially available in multiple sizes and shapes, and can vary according to individual needs. Without limitation, the common names for the variety of externally worn sanitary napkin products include pantyliners, full-size pads, and ultrathins. The majority of sanitary napkins are either rectangular or hourglass shaped to fit in the crotch of undergarments. Most products are attached directly to a user's undergarment, and contact the perineum intimately when the undergarments are pulled up. Alternatively, sanitary napkins can be attached directly to the body with body adhering adhesives, or held in place against the body from pressures exerted by the labia.

Many of the incremental changes that have evolved in the development of new sanitary napkins are targeted to improve protection of the products. Compressive forces acting on the pads from body position and activity, can distort the pad in proximity of the vaginal opening, resulting in a limited area for the fluid to contact the product when exiting the vaginal opening. Therefore, lateral extensions, commonly referred to as wings, accompany many products in an effort to reduce leakage that can occur due to the reduced area. The lateral extensions also act to keep the sanitary napkin in the location it was originally placed. Lateral extensions can be both flexible and stiff, can contain adhesive or not, can be wrapped around the underside of undergarments, can attach to the underside of undergarments, or can be held against or attached to the body. Sanitary napkins typically contain two lateral extensions, but one of ordinary skill in the art, would recognize that more than two lateral extensions could be used to enhance a product's performance.

Sanitary napkins typically are packaged loosely into a primary package, such as a box or bag, and can have secondary packaging that allows the consumer to transport individual products and protect them from any unwanted environmental affects. The individually packaged napkins are often times folded and then wrapped to facilitate the ease and discretion of transporting the products. Products and methods of individually folded and wrapped sanitary products are disclosed in U.S. Pat. No. 4,556,146 and 4,917,675; both of which are herein incorporated by reference.

Sanitary napkins are typically made from a number of separate elements. A simplistic configuration would include the following elements: a liquid permeable material representing the body-contacting surface, a liquid impermeable material representing a barrier as the opposite surface, and an absorbent material or combination of absorbent materials contained between the two surface defining materials. Adhesives can be added, with or without the presence of heat and pressure, to adhere the separate elements to one another. Adhesives can also be applied to the outer surfaces of the product for either attaching to undergarments, or directly to the body. A transfer layer or material may optionally be placed between the liquid permeable material and the absorbent material(s) to improve the transfer of fluid into the absorbent materials. The foregoing statements are intended to describe the basic elements contained within the majority of sanitary napkins commercially available; however, the present invention is not limited to disposable absorbent articles comprising the disclosed elements. The art is replete with many additional technologies aimed towards improving the performance and comfort of sanitary napkins, all of which would not alter the utility of the present invention.

The liquid permeable material may be a nonwoven fabric such as a spunbonded fabric, a thermal bonded fabric, a resin bonded fabric, and the like; an apertured polymeric film such as DRI-WEAVE commercially available from the Procter and Gamble Company, and the like; or any other suitable covering surface that is capable of allowing fluid to permeate and be comfortably worn against the perineum. The fibrous structures can be coated with essential oils, or a solution of essential oils, as the individual fibers are spun, or during, or after a nonwoven structure is made with the fibers. Polymeric films can be coated with essential oils by any number of methods known by one skilled in the art. The preferred material to be used as the body-contacting surface is a non-woven.

After menstrual fluid or urine contacts the cover of the napkin, the fluid is transferred from the cover material to the absorbent materials for storage. This can include the use of an additional transfer layer to facilitate the kinetics of this step. A representative, non-limiting list of materials useful as the absorbent includes cellulosic fibers, such as wood pulp and cotton pulp; synthetic fibers, such as polyesters and polyolefms; superabsorbent polymers, such as polyacrylic acid, and the like. Another unexpected benefit of the present invention is that it has been found that essential oils can be added to superabsorbent polymers without significant premature swelling of the polymers. Preferably, the structure includes wood pulp and about 5 to 80% fusible, thermoplastic fibers. As with the cover materials, essential oils can be added to the absorbent materials during their manufacture.

To prevent any absorbed fluid from leaking out of the bottom of the napkin and onto the body or clothing, a liquid impermeable material is added as a barrier. Useful barriers include, without limitation, polymeric films or coatings, such as polyolefins (e.g., polyehtylene and polypropylene), polyvinyls (e.g., polyvinyl acetate, polyvinyl chloride, and poyvinylidene chloride), copolymers (e.g., ethylene vinyl acetate), and blends or laminates of one or more of the above polymers; bodily fluid repellant structures such as nonwovens, apertured flims, and repellant fiber layers integrated into the bottom layer of the absorbent materials. Preferred barriers include polypropylene and bodily fluid repellant nonwovens. The most preferred barrier is constructed out of polypropylene films. Without limitation, two methods to apply essential oils to the preferred barrier materials is by externally coating the materials, or by compounding in essential oils prior to fiber or film extrusion, after which the essential oils will migrate to the surface of the materials.

Adhesives are often times included in the construction of disposable absorbent articles, e.g., sanitary napkins to adhere the multiple, or plurality of, elements described above. Positioning adhesive can also be applied to the impermeable barrier material, allowing the sanitary napkin to be attached to the crotch of undergarments. To eliminate gaps between the body and the sanitary napkin, there has also been innovations disclosing methods of using adhesives on portions of the liquid permeable surface for attaching the napkins directly to the perineum. A direct body adhering sanitary napkin is disclosed in U.S. Pat. No. 5,658,270, herein incorporated by reference. Adhesives are excellent carriers for essential oils. The additive can readily be dispersed in many adhesive types, such as hot melts and warm melts. Using adhesives as a carrier can improve the add-on level and placement of essential oils. The adhesives also serve as binder material that can reduce the amount of essential oils lost prior to use. A representative, non-limiting list of materials useful as either construction or positioning adhesives includes acrylics, starch based hot melts, adhesives based on block copolymers of vinyl aromatic hyrdocarbon and one or more conjugated diene or hyrogenated aliphatic blocks, polylactic acids, hot melts based polyolefins such as amorphous poly alpha olefins which may consist of one or more of the following monomers: propylene, ehtylene, butene, and hexene; hot melts based on low density polyethylene or low density polyethylene copolymers including ethylene vinyl acetate, methyl acrylate, n-butyl acrylate, and acrylic acid. Typical positioning adhesives that are well known in the art are based styrenic block copolymers as disclosed in U.S. Pat. Nos. 5,149,741; 5,143,968; and 5,057,571.

It is also possible for the material used for wrapping the individual products, e.g, disposable absorbent articles, to contain an effective amount of essential oils to provide an aroma and inhibit microbial growth, e.g., from about 0.1 to about 8.0 weight percent. Typically the wrapping material is constructed with either polyolefin films, such as polypropylene, or with a form of paper. One method of utilizing the wrapping material to apply essential oils to the napkin, is to coat the paper or polymeric film with known techniques, such as spraying, slot coating, or extrusion. The essential oils can then be transferred or migrate to the napkin itself during the packaging process or anytime prior to the consumer opening the individually packaged product.

The disclosure thus far has focused on sanitary napkins, the multitude of elemental features that can be included in their construction, and methods of adding essential oils to one or more of the individual elements. The essential oils can be added to sanitary napkins during their manufacture, or to the final product. Adding the essential oils during the article manufacture is the most preferred method of incorporation of the present invention. This approach can be accomplished through a number of techniques, including but not limited to, spraying, slot coating, transfer coating, solid gravimeteric feeders, via positioning adhesives and construction adhesives, and dip coating. Preferably, essential oils are applied by spraying onto the sanitary napkin during its manufacture.

Essential oils can also be added to tampons, and other internally worn disposable absorbent articles. Consistent with the techniques for incorporating essential oils into externally worn articles, there are multiple methods suitable for the present invention, including, but not limited to adding essential oils to an element used to manufacture tampons, adding essential oils to a tampon during its manufacture, and adding essential oils to the tampon after its manufacture. The majority of tampons are constructed of absorbent fibers, such as viscose rayon and cotton, and the like. The tampons may optionally have a cover material on the outside surface to provide ease of insertion and removal, and also to reduce fiber sloughing during use in the vaginal canal. A representative, non-limiting list of materials useful as the cover includes apertured polymeric films, nonwovens constructed from polyester fibers, polyolefin fibers, bicomponent fibers, and the like; and other materials that will allow fluid to pass through and into the absorbent material contained by the cover. U.S. Pat. No. 4,294,253 and 4,642,108 disclose tampon constructions and processes of manufacture.

Preferably, essential oils would be added to the tampon cover material. The technique for adding the essential oils to the cover could be any known in the art, such as dip, slot, spray, melt blown, control coat, and swirl spray.

Another disposable absorbent article the present invention is appropriate for is wipes or towelettes. Wipes are typically in the form of a fibrous web constructed from a single layer of fibers, or multiple layers. The fibers can be woven or nonwoven in nature. Preferably the construction is a nonwoven made from spunbound, meltblown, or combination thereof. A representative, non-limiting list of materials useful in manufacturing the non-wovens is polyolefins, polyesters, acrylics, and cotton. Wipes are used for numerous fluid management purposes, including, but not limited to during baby diaper changes, during menses management article changes, after urination, after a bowel movement, and after sexual intercourse. Those of ordinary skill in the art would readily appreciate that a wipe containing an effective amount of essential oil to provide a pleasant aroma and inhibit microbial growth, would be beneficial for the above purposes.

EXAMPLES

In the following examples, a series of essential oils were subjected to the zone of inhibition test with a variety of bacteria as follows. The selected bacterium, as shown in Table 1 below, was uniformly added to a medium such as blood or nutrient agar. An essential oil was added to a small stainless steel cylinder embedded in the agar, and incubated overnight. The size of the bacteria-free zones around the cylinders were then measured. Typically, multiple cylinders, with varying levels of the agent, were used. Table 1 shows the results for a number of essential oils when tested with various bacteria test cultures.

TABLE 1

Zone of Inhibition

| Essential Oil type, 0.1 ml. | S. aureus ATCC 6538 | E. coli ATCC 8739 | Ps. aeruginosa ATCC 9027 | Str. faecalis ATCC 7080 | C. albicans ATCC 10231 |
|---|---|---|---|---|---|
| Rosemary | 36 | 24 | 18 | 23 | 20 |
| Clove bud | 30 | 21 | 17 | 17 | 19 |
| Ginger | 16 | 12 | 12 | 14 | 10 |
| Thulasi | 27 | 20 | 16 | 17 | 20 |
| Turmeric | 21 | 14 | 15 | 13 | 9 |
| Lemon grass | 25 | 18 | 17 | 18 | 19 |

A series of essential oils were also subjected to the Durham's fusion tube test using a variety of bacteria. The tests were conducted as follows. Agar slants were innoculated with the desired culture, and a measured amount of hexane extracted essential oil (i.e., 0.1 ml) was placed in a sterile Durham's Fusion tube (2 mm inner diameter). The Durham's tube was introduced to the agar slant and incubated at a 30° angle such that the vapors emerging from the tube covered the surface of the agar slant.

Table 2 shows the percent inhibition of the volatile component of selected essential oils after 48 hours of residence in the innoculated agar slant.

Tables 3 and 4 show the minimum inhibitory concentrations for Hinoki Oil and Achillea Oil, using the Durham's fusion tube method.

TABLE 2

Durham's Fusion Test

Inhibition after 48 hours

| Essential Oil type, 0.1 ml. | S. aureus ATCC 6538 | E. coli ATCC 8739 | Ps. aeruginosa ATCC 9027 | Str. faecalis ATCC 7080 | C. albicans ATCC 10231 |
|---|---|---|---|---|---|
| Rosemary | ++++ | – | – | ++++ | ++ |
| Clove bud | – | – | – | – | – |
| Ginger | – | – | – | + | + |
| Thulasi | – | – | – | – | – |
| Turmeric | – | – | – | – | – |
| Lemon grass | – | – | – | – | – |
| Thyme | ++ | + | – | Not tested | – |

Key inhibition gradient:
– = 0% inhibition on start
+ = 25% inhibition
++ = 50% inhibition
+++ = 75% inhibition
++++ = 100% inhibition

TABLE 3

Hinoki Oil: Minimum Inhibition Concentrations

| Conc. ppm | Ps. aeruginosa ATCC 9027 | Proteus vulgaris | S. aureus ATCC 6538 | C. albicans ATCC 10231 | L. acidophillus ATCC 4356 | P. mirabilis ATCC 29906 | E. coli ATCC 8739 |
|---|---|---|---|---|---|---|---|
| 400 | + | + | + | + | + | + | + |
| 600 | + | + | + | + | + | + | + |
| 800 | + | + | + | + | + | + | + |
| 1000 | + | + | − | + | − | + | + |
| 1100 | + | + | − | + | − | + | + |
| 1200 | + | + | − | + | − | + | + |
| 1600 | + | + | − | + | − | + | + |
| 1800 | + | + | − | + | − | + | + |
| 2000 | + | + | − | + | − | + | + |
| 2400 | − | − | − | + | − | − | + |
| 2600 | − | − | − | + | − | − | + |
| 2800 | − | − | − | + | − | − | + |
| 3000 | − | − | − | + | − | − | + |

TABLE 4

Achillea Oil: Minimum Inhibition Concentrations

| Conc. ppm | Ps. aeruginosa ATCC 9027 | Proteus vulgaris | S. aureus ATCC 6538 | C. albicans ATCC 10231 | L. acidophillus ATCC 4356 | P. mirabilis ATCC 29906 | E. coli ATCC 8739 |
|---|---|---|---|---|---|---|---|
| 400 | + | + | + | + | + | + | + |
| 600 | + | + | + | + | + | + | + |
| 800 | + | + | + | + | + | + | + |
| 1000 | + | + | + | + | + | + | + |
| 1100 | + | + | − | + | − | + | + |
| 1200 | + | + | − | + | − | + | + |
| 1600 | + | + | − | + | − | + | + |
| 1800 | + | + | − | + | − | + | + |
| 2000 | + | + | − | + | − | + | + |
| 2400 | + | + | − | + | − | + | + |
| 2600 | + | + | − | + | − | − | + |
| 2800 | + | − | − | + | − | − | + |
| 3000 | + | − | − | + | − | − | + |

The invention has been illustrated by, but is not intended to be limited to, the above description and examples. The scope of the invention is to be determined by the claims attached hereto.

What is claimed is:

1. A method of making a disposable absorbent article comprising the following steps:
    a) providing an absorbent material,
    b) providing a liquid permeable material,
    c) providing a liquid impermeable material,
    d) encasing the absorbent material with the liquid permeable material and liquid impermeable material; and
    e) contacting at least one of the absorbent material, the liquid permeable material, the liquid impermeable material, or a combination thereof with an effective amount of essential oil to provide an aroma and inhibit microbial growth.

2. The method of claim 1 wherein the process of contacting any one of said materials with essential oil is selected from the group consisting of dip, slot, spray, roll, and swirl.

3. The method of claim 1 wherein the amount of essential oil is from about 0.1 to about 8.0 weight percent.

4. The method of claim 1 further comprising the step of adhering the absorbent material to the liquid permeable material, or the absorbent material to the liquid impermeable layer with adhesives.

5. The method of claim 4 wherein said essential oil is found in the adhesives, in an amount effective to provide an aroma and inhibit microbial growth.

6. The method of claim 1 wherein the absorbent material contains superabsorbents.

7. The method of claim 6 wherein said essential oil is found in the superabsorbents, in an amount effective to provide an aroma and inhibit microbial growth.

* * * * *